US00PP16089P2

(12) United States Plant Patent
Post

(10) Patent No.: US PP16,089 P2
(45) Date of Patent: Nov. 1, 2005

(54) ***CHRYSANTHEMUM* PLANT NAMED 'ESPINAL'**

(50) Latin Name: *Chrysanthemum×morifolium*
Varietal Denomination: Espinal

(75) Inventor: Arie Gerard Post, 's-Gravenzande (NL)

(73) Assignee: Deliflor Royalties B.V., Maasdijk (NL)

( * ) Notice: Subject to any disclaimer, the term of this patent is extended or adjusted under 35 U.S.C. 154(b) by 46 days.

(21) Appl. No.: 10/915,051

(22) Filed: Aug. 10, 2004

(51) Int. Cl.[7] ..... A01H 5/00
(52) U.S. Cl. ..... Plt./289
(58) Field of Search ..... Plt./289

(56) References Cited

U.S. PATENT DOCUMENTS

PP6,886 P * 6/1989 VandenBerg ..... Plt./289
PP7,406 P * 12/1990 VandenBerg ..... Plt./289
PP12,922 P2 * 9/2002 Vandenberg ..... Plt./289
PP13,133 P2 * 10/2002 Vandenberg ..... Plt./289
PP15,116 P2 * 8/2004 Dekker ..... Plt./289
2002/0092063 P1 * 7/2002 Noodelijk ..... Plt./289
2002/0092064 P1 * 7/2002 Vandenberg ..... Plt./289
2002/0092065 P1 * 7/2002 Vandenberg ..... Plt./289

* cited by examiner

*Primary Examiner*—Kent Bell
*Assistant Examiner*—W. C. Haas

(74) *Attorney, Agent, or Firm*—C. A. Whealy

(57) ABSTRACT

A new and distinct cultivar of *Chrysanthemum* plant named 'Espinal', characterized by its pompon-type inflorescences with golden yellow-colored ray florets; freely branching habit; freely flowering habit; early and uniform flowering response; and good postproduction longevity.

1 Drawing Sheet

Botanical designation: *Chrysanthemum×morifolium.*
Variety denomination: 'Espinal'.

BACKGROUND OF THE INVENTION

The present invention relates to a new and distinct cultivar of *Chrysanthemum* plant, botanically known as *Chrysanthemum×morifolium* and referred to by the name 'Espinal'.

The new *Chrysanthemum* is the product of a planned breeding program conducted by the Inventor in 's Gravenzande, The Netherlands. The objective of the breeding program is to create new vigorous cut *Chrysanthemum* cultivars with interesting inflorescence forms and attractive floret coloration.

The new *Chrysanthemum* originated from an open-pollination in March, 1995 in 's Gravenzande, The Netherlands, of two unknown selections of *Chrysanthemum×morifolium*. The new *Chrysanthemum* was discovered and selected by the Inventor as a single plant within the progeny of the stated open-pollination in a controlled environment in 's Gravenzande, The Netherlands.

Asexual reproduction of the new *Chrysanthemum* by terminal cuttings harvested in 's Gravenzande, The Netherlands since Oct. 10, 1998, has shown that the unique features of this new *Chrysanthemum* are stable and reproduced true to type in successive generations.

BRIEF SUMMARY OF THE INVENTION

The cultivar Espinal has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Espinal'. These characteristics in combination distinguish 'Espinal' as a new and distinct cultivar:

1. Pompon-type inflorescences with golden yellow-colored ray florets; typically grown as a spray type.
2. Freely branching habit.
3. Freely flowering habit.
4. Early and uniform flowering response.
5. Good postproduction longevity.

Plants of the new *Chrysanthemum* can be compared to plants of the *Chrysanthemum* cultivar Verburgh (U.S. Plant Pat. No. 15,116). In side-by-side comparisons conducted in 's Gravenzande, The Netherlands, plants of the new *Chrysanthemum* differed primarily from plants of the cultivar Verburgh in the following characteristics:

1. Plants of the new *Chrysanthemum* had more leaves per stem than plants of the cultivar Verburgh.
2. Plants of the new *Chrysanthemum* were more freely flowering than plants of the cultivar Verburgh.
3. Plants of the new *Chrysanthemum* flowered about five days earlier than plants of the cultivar Verburgh.
4. Plants of the new *Chrysanthemum* had fewer ray florets per inflorescence than plants of the cultivar Verburgh.

Plants of the new *Chrysanthemum* can also be compared to plants of the *Chrysanthemum* cultivar Focus (U.S. Plant Pat. No. 13,133). In side-by-side comparisons conducted in 's Gravenzande, The Netherlands, plants of the new *Chry-*

*santhemum* differed primarily from plants of the cultivar Focus in the following characteristics:

1. Plants of the new *Chrysanthemum* had shinier leaves than plants of the cultivar Focus.
2. Plants of the new *Chrysanthemum* were more freely flowering than plants of the cultivar Focus.
3. Plants of the new *Chrysanthemum* had larger inflorescences than plants of the cultivar Focus.
4. Plants of the new *Chrysanthemum* and the cultivar Focus differed in ray floret coloration.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Chrysanthemum.*

The photograph at the top of the sheet comprises a side perspective view of a typical flowering stem of 'Espinal'.

The photograph at the bottom left of the sheet comprises a close-up view of upper surface of a typical leaf and a typical inflorescence of 'Espinal'.

The photograph at the bottom right of the sheet comprises a close-up view of lower surface of a typical inflorescence and a typical leaf of 'Espinal'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown during the winter and early spring in 's Gravenzande, The Netherlands, under commercial practice in a glass-covered greenhouse. Plants were initially given long day/short night treatments followed by short day/long night treatments to induce flower initiation and development. During the production of the plants, day and night temperatures averaged 18° C. and light levels were about 4,000 lux. Plants were pinched once and were about ten weeks from planting when the photographs and the description were taken.

Botanical classification: *Chrysanthemum×morifolium* cultivar Espinal.

Commercial classification: Pompon-type *Chrysanthemum* typically grown as a spray-type cut flower.

Parentage: Open-pollination of two unknown selections of *Chrysanthemum×morifolium.*

Propagation:

*Type.*—Terminal tip cuttings.

*Time to initiate roots, summer.*—About 5 days at 20° C.

*Time to initiate roots, winter.*—About 6 days at 18° C.

*Time to produce a rooted cutting, summer.*—About 10 days at 20° C.

*Time to produce a rooted cutting, winter.*—About 14 days at 18° C.

*Root description.*—Fine and freely branching; white in color.

Plant description:

*Appearance.*—Herbaceous pompon-type cut *Chrysanthemum*; typically grown as a spray-type; erect and strong flowering stems.

*Growth rate.*—Moderate; moderately vigorous.

*Flowering stem description.*—Length: About 70 to 80 cm. Diameter: About 6 mm. Strength: Strong. Aspect: Erect. Branching habit: Freely branching, about 10 to 15 lateral branches develop per plant. Lateral branches about 9 to 19 cm in length. Color: 146B.

*Foliage description.*—Arrangement: Alternate. Length: About 6 to 11 cm. Width: About 4 to 7 cm. Apex: Cuspidate. Base: Truncate. Margin: Pinnately lobed; serrate. Texture, upper and lower surface: Pubescent. Petiole length: About 2 to 3 cm. Color: Developing and fully expanded foliage, upper surface: 147A. Developing and fully expanded foliage, lower surface: Between 137C and 147B. Venation, upper surface: 147C. Venation, lower surface: 146C. Petiole, upper and lower surfaces: 137C.

Inflorescence description:

*Appearance.*—Pompon-type inflorescence form with elongated ovate-shaped ray florets. Inflorescences borne on terminals above foliage. Disk and ray florets develop acropetally on a capitulum. Not fragrant. Typically grown as a spray-type.

*Flowering response.*—Under natural conditions, plants typically flower in November in the Northern Hemisphere. At other times of the year, inflorescence initiation and development can be induced under short day/long night conditions (at least 13.5 hours of darkness). Plants exposed to long day/short night conditions after planting followed by photoinductive short day/long night conditions flower about 47 days later. Early and uniform flowering response.

*Postproduction longevity.*—Cut inflorescences will maintain good substance and form for about three weeks.

*Quantity of inflorescences per flowering stem.*—About 15 to 20 inflorescences per flowering stem.

*Inflorescence size.*—Diameter: About 4 to 5 cm. Depth (height): About 1.5 to 2 cm. Diameter of disc: About 6 mm.

*Inflorescence buds.*—Length: About 8 to 9 mm. Diameter: About 9 to 11 mm. Shape: Oblate. Color: 145A to 143C.

*Ray florets.*—Length: About 1.5 to 2.3 cm. Width: About 7 to 10 mm. Shape: Elongated ovate. Apex: Acute. Base: Fused, short corolla tube. Margin: Entire. Texture, upper and lower surfaces: Smooth, glabrous. Number of ray florets per inflorescence: About 250. Color: When opening, upper surface: 9A. When opening, lower surface: 6B. Fully opened, upper surface: 6A; color becoming closer to 5A with development. Fully opened, lower surface: 6C overlain slightly with 22A.

*Disc florets.*—Shape: Tubular. Length: About 5 mm. Width: About 1 mm. Number of disc florets per inflorescence: About 20 to 25. Color: Immature: 145C. Mature: Apex: 144C. Mid-section: 13B. Base: 145D.

*Peduncles.*—Length, terminal peduncle: About 7 cm. Length, fourth peduncle: About 9 cm. Diameter: About 2 to 3 mm. Strength: Moderately strong. Texture: Pubescent. Color: Closest to 146B.

*Reproductive organs.*—Androecium: Present on disc florets only. Gynoecium: Present on both ray and disc florets.

*Seed/fruit.*—Seed and fruit production has not been observed.

Disease/pest resistance: Resistance to known *Chrysanthemum* pathogens and pests has not been observed on plants of the new *Chrysanthemum.*

It is claimed:

1. A new and distinct cultivar of *Chrysanthemum* plant named 'Espinal', as illustrated and described.

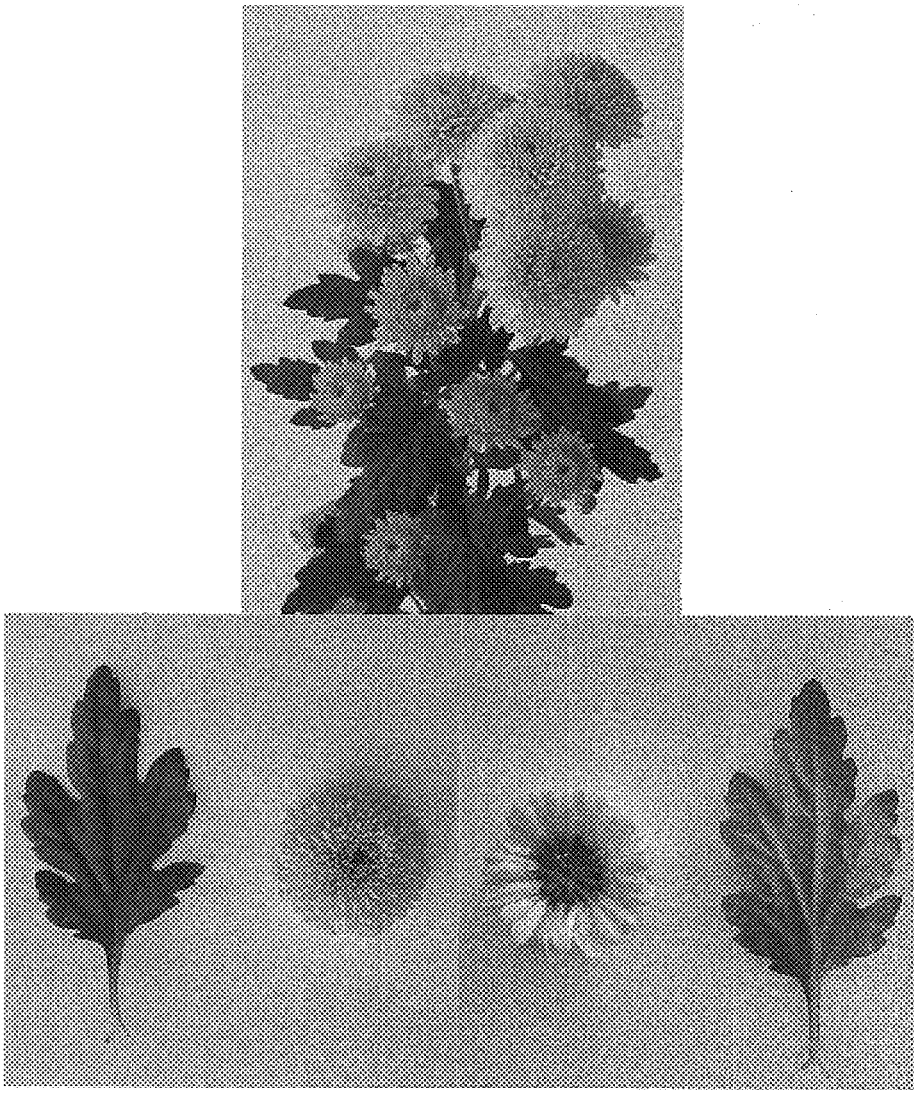

* * * * *